United States Patent [19]
Schwender

[11] 3,936,454
[45] Feb. 3, 1976

[54] 5-AMINO-4-CHLORO-6-(SUBSTITUTED AMINO)-PYRIMIDINES

[75] Inventor: Charles F. Schwender, Lebanon, N.J.

[73] Assignee: Warner-Lambert Company, Morris Plains, N.J.

[22] Filed: Aug. 5, 1974

[21] Appl. No.: 494,661

Related U.S. Application Data

[62] Division of Ser. No. 388,290, Aug. 14, 1973, Pat. No. 3,862,189.

[52] U.S. Cl. .................... 260/256.4 N; 260/256.4 F; 260/256.5 R; 424/251
[51] Int. Cl.² ...................................... C07D 239/26
[58] Field of Search ........................... 260/256 HN

[56] References Cited
UNITED STATES PATENTS 3,407,202  10/1968  Pachter et al. ............... 260/256.4 N
3,499,898   3/1970  von Bebenburg et al. .... 260/256.4 N Primary Examiner—Richard J. Gallagher
Assistant Examiner—James H. Turnipseed
Attorney, Agent, or Firm—Albert H. Graddis; Frank S. Chow

[57] ABSTRACT

The present invention relates to compounds having the following formula:

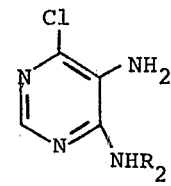

in which $R_2$ is naphthyl alkyl of 1 to 3 carbons or phenyl alkyl of 1 to 3 carbons substituted in the aryl moiety by one or two alkoxy of 1 to 6 carbons, or one or two chloro. This compound is useful as an intermediate for the production of the compounds of the formula:

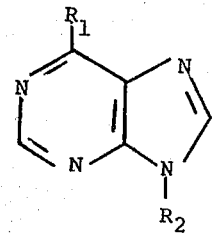

which are useful as antianginal or bronchodilator agents.

5 Claims, No Drawings

5-AMINO-4-CHLORO-6-(SUBSTITUTED AMINO)-PYRIMIDINES

This is a division of application Ser. No. 388,290 filed Aug. 14, 1973 now U.S. Pat. No. 3,862,189 issued Jan. 21, 1975.

The present invention is concerned with novel compounds and, more particularly, the present invention is concerned with aralkyl-substituted purines and pyrimidines having structural formula I:

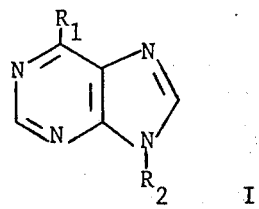

wherein $R_1$ is hydroxy, methoxy, mercapto, hydrazino, substituted hydrazino, chloro, amino, alkylamino, dialkylamino, hydroxyalkylamino, aralkylamino or substituted aralkylamino and $R_2$ is phenylalkyl having 1 to 3 carbon atoms in the alkyl moiety and at least two alkoxy, alkyl, halogen, hydroxy, nitro, amino, substituted amino, aminomethyl, acylamino, carboxy, carboxyalkyl or hydroxymethyl groups in the benzene ring or naphthylalkyl, tetrahydronaphthylalkyl, quinolylalkyl, tetrahydroquinolylalkyl or isoquinolylalkyl, each having 1 to 3 carbon atoms in the alkyl moiety and pharmaceutically acceptable acid addition salts thereof.

In addition, esters or amides of the above compounds utilizing alkanoyl or aralkanoyl, such as acetyl, propionyl, benzoyl, succinoyl and the like, and the pharmaceutically acceptable acid addition salts are also within the scope of this invention.

In the above definitions for $R_1$, the term "alkyl" means an aliphatic hydrocarbon having 1 to 6 carbon atoms, for example, methyl, propyl, isopropyl, isobutyl and the like. The term "aryl" denotes an aromatic hydrocarbon having 6 to 14 carbon atoms, for example, phenyl, naphthyl, anthryl and the like. The term "aralkyl" designates a combination of the hereinbefore defined alkyl and aryl groups. Substituted hydrazino denotes hydrazino substituted on either nitrogen atom or both nitrogen atoms by one or more alkyl or aryl groups.

In the above definitions for $R_2$, the term "alkyl" stands for an aliphatic hydrocarbon of 1 to 6 carbon atoms, unless otherwise specified, and applies to the alkyl residues of the alkoxy and acyl moieties. Substituted amino includes within its scope amino groups substituted by alkyl and aryl groups defined in the preceding paragraph. Halogen encompasses all of the halo groups, chloro, bromo, iodo and fluoro.

Among the preferred compounds of this invention are those purine derivatives wherein $R_1$ is chloro, amino, hydroxy, hydrazino, n-propylamino or 2-hydroxyethylamino and $R_2$ is dimethoxybenzyl and $R_1$ is amino and $R_2$ is dichlorobenzyl, 3,4-dimethylbenzyl.

The compounds of this invention exhibit a unique mode of biological action in that they produce selective dilation of certain coronary arteries causing a redistribution of blood flow towards ischemic areas of the heart enhancing perfusion and reducing anoxia which cause anginal pains. This biological activity is demonstrated in accordance with the procedure described in J. Pharmacol. Exp. Ther., 176,184 (1971). Only nitroglycerin and some β-adrenergic blockers have been demonstrated to similarly redistribute blood flow to ischemic areas by large coronary artery dilation. See Eur. J. Pharmacol., 16, 271 (1971). The compounds of this invention offer an advantageous treatment of angina without interference with adrenergic control of the heart or without resorting to the use of nitrates.

Existing coronary vasodilators such as dipyridamole and chromonar dilate smaller vessels increasing coronary blood flow without redistributing flow to needed ischemic areas. In severe ischemia, dipyridamole actually induced anginal attacks in man since it diverted blood flow away from ischemic areas through its dilator action on smaller coronary vessels. See Ann. Rep. Med. Chem., 7, 69 (1972).

Experimentally, this blood flow redistribution is demonstrable in a dog by measuring changes in resistance to blood flow of larger coronary arteries (RL) relative to small vessel physical resistance to flow (RT), using the protocol described in J. Pharmacol. Exp. Ther., 176, 184 (1971).

Generally, the compounds of this invention at a dose of about 1–10 mg/kg were observed to effect a drop in the RL:RT ratio. Known coronary vasodilators such as dipyridamole and chromonar caused an increased RL:RT ratio reflecting a redistribution of blood flow away from ischemic tissues.

The compounds of this invention, particularly the preferred species, are indicated in the management of angina pectoris. A usual dose of 1–10 mg/kg by injection or orally two or three times daily is suggested to prevent anginal attack. These compounds can be administered by combining with excipients such as lactose or water for injection.

In addition to the antianginal effects described above, the compounds of this invention were also observed to protect guinea pigs from histamine-induced bronchial spasm. Thus tested in accordance with the procedure described in J. Pharmacol. Exp. Ther., 90, 254 (1947) at a dose of 1–50 mg/kg intraperitoneally, they were effective to protect the guinea pigs against bronchial spasms which had been induced by the administration of one mg of histamine. At this dosage level, a mild cardiotonic effect was also observed. Hence, the compounds of this invention are also useful in the treatment of bronchial spasms such as in bronchial asthma. Generally speaking, a dose of 1–50 mg/kg administered orally or by intramuscular injection is suggested.

According to the present invention, the above compounds are prepared by processes as illustrated in the following reaction scheme:

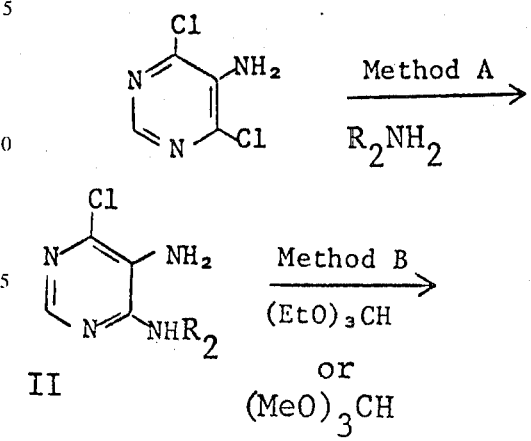

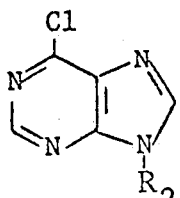

III

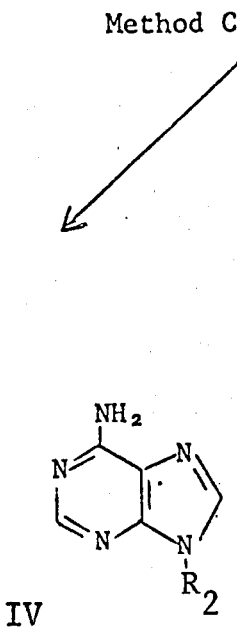

Method C
NH₃

IV resultant substituted amino pyrimidine II is cyclized with triethyl or trimethyl orthoformate to the 6-chloropurine derivative III as in Method B. Treating said 6-chloropurine derivative with ammonia as brought out in Method C, or an appropriate nucleophile as in Method D, gives the 6-substituted purine derivative I.

The starting material for the first process, 5-amino-4,6-dichloropyrimidine, is available from commercial chemical suppliers such as Krishell Laboratories, Inc. The amino compounds utilized in Method A, triethyl- and trimethyl orthoformate of Method B and the nucleophiles of Method D are available from the Aldrich Chemical Company or readily prepared by methods well known to those skilled in the art.

In addition, treatment of adenine with a substituted benzyl or aralkyl halide in the presence of a base such as sodium hydride gives the desired 9-substituted adenine directly. This reaction is illustrated by the following reaction scheme:

Method D
Nucleophile

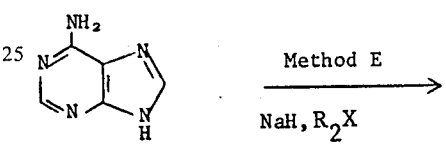

Method E
$\longrightarrow$
NaH, $R_2X$

I

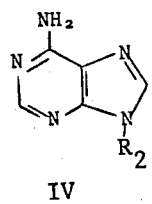

IV

Adenine, the starting material for the second process is commercially available from the Aldrich Chemical Company as are the requisite aralkyl halides, $R_2X$.

The following experiments are general procedures for the preparation of the compounds of this invention: all temperatures are in degrees centigrade.

Referring now to the reaction scheme, in Method A 5-amino-4,6-dichloropyrimidine is condensed with a substituted amine in butanol and triethylamine. The

TABLE 1

| R | Formula | Analysis* | mp°C | Recrystallization Solvent | Method Preparation |
|---|---|---|---|---|---|
| CH₂-C₆H₃(OCH₃)₂ (2,3-dimethoxybenzyl) | C₁₃H₁₅ClN₄O₂ | CHNCl | 188–191 | MeOH/H₂O | A |
| CH₂CH₂-C₆H₃(OCH₃)₂ | C₁₄H₁₇ClN₄O₂ | CHNCl | 133–135 | MeOH/H₂O | A |
| CH₂-naphthyl | C₁₅H₁₃ClN₄ | CHNCl | 219–223 | MeOH/H₂O | A |
| CH₂-C₆H₃Cl₂ | C₁₁H₉Cl₃N₄ | CHNCl | 197–198.5 | EtOH/H₂O | A |

*Compounds reported analyzed within ±0.4% of theory.

TABLE II

[Structure: purine ring with $R_1$ at 6-position and $R_2$ at 7-position (N)]

| $R_1$ | $R_2$ | Formula | Analysis* | mp°C | Solvent Recrystallization | Method Preparation |
|---|---|---|---|---|---|---|
| Cl | CH₂-(3,4-dimethoxyphenyl) | C₁₄H₁₃ClN₄O₂ | CHNCl | 160–164 | EtOH/H₂O | B |
| SH | CH₂-(3,4-dimethoxyphenyl) | C₁₄H₁₄N₄O₂S | CHNS | 200–205 | DMF/ether | D and thiourea |
| NHCH₂-(naphthyl) | '' | C₂₅H₂₃N₅O₂ | CHN | 150–153 | acetone/hexane | D |
| NH₂ | CH₂-(3,4-dimethoxyphenyl) | C₁₄H₁₅N₅O₂ | CHN | 192–194 | EtOH/H₂O | C |
| OH | CH₂-(3,4-dimethoxyphenyl) | C₁₄H₁₄N₄O₃ | CHN | 200–202 | MeOH | D and HCl, dilute |
| HNCH₂-(phenyl) | CH₂-(3,4-dimethoxyphenyl) | C₂₁H₂₁N₅O₂ | CHN | 165–167 | EtOH | D |
| NHCH₂CH₂OH | '' | C₁₆H₁₉N₅O₃ | CHN | 144–146 | 2-PrOH | D |
| OCH₃ | CH₂-(3,4-dimethoxyphenyl) | C₁₅H₁₆N₄O₃ | CHN | 129–132 | 2-PrOH | D |
| NHNH₂ | '' | C₁₄H₁₆N₆O₂ | CHN | 181–184 | EtOH | D |
| NHCH₂CH₂CH₃ | '' | C₁₇H₂₁N₅O₂ | CHN | 123–125 | acetone | D |
| Cl | CH₂CH₂-(3,4-dimethoxyphenyl) | C₁₅H₁₅ClN₄O₂ | CHNCl | 116–119 | CCl₄/heptane | B |
| NH₂ | '' | C₁₅H₁₇N₅O₂ | CHN | 194–197 | benzene/heptane | C |
| Cl | CH₂-naphthyl | C₁₆H₁₁ClN₄ | CHNCl | 156–158 | MeOH | B |
| NH₂ | '' | C₁₆H₁₃N₅ | CHN | 269–272 dec | EtOH | C |
| NHCH₂CH₂CH₃ | '' | C₁₉H₁₉N₅ | CHN | 161.5–163.5 | MeOH/H₂O | D |
| NHCH₂CH₂OH | '' | C₁₈H₁₇N₅O | CHN | 199.5–200 | EtOH/H₂O | D |
| NH₂ | '' | C₁₄H₁₅N₅ | CHN | 211–213 | CH₃OH | F |
| Cl | CH₂-(3,4-dimethylphenyl) | C₁₂H₇Cl₃N₄ | CHNCl | 141–143 | EtOH/H₂O | B |
| NH₂ | CH₂-(3,4-dichlorophenyl) | C₁₂H₉Cl₂N₅ | CHNCl | 255–258 | EtOH/H₂O | C |

References
1. M. M. Winbury, B. B. Howe, H. R. Weiss, J. Pharmacol. Exp. Ther., 176, 184 (1971).
2. M. M. Winbury, H. R. Weiss and B. B. Howe, Eur. J. Pharmacol., 16, 271 (1971).
3. H. R. Weiss and M. M. Winbury, Fed. Proc., 30 (2) 631 (1971).
4. O. Mantero and F. Conti, Circulatory Drugs, A. Bertelli, ed. pp 118–123, North-Holland, Amsterdam, The Netherlands, 1969.
5. C. F. Schwender, "Antianginal Agents", Ann. Rep. Med. Chem., 7, 69, R. V. Heinzelmann, ed. Academic Press, New York, 1972.
O. H. Siegmund, H. R. Granger and A. M. Lands, J. Pharmacol. Exp. Ther., 90, 254 (1947).
*Satisfactory analysis within ±0.4% of theoretical was obtained for all compounds reported

METHOD A

5-Amino-4-chloro-6-(3,4-dimethoxybenzylamino)-pyrimidine

A reaction mixture containing 1.00 g (6.09 mmols) of 4,6-dichloro-5-aminopyrimidine, 1.22 g (7.30 mmols) of 3,4-dimethoxybenzylamine, 1.02 ml (7.30 mmols) of triethylamine and 35 ml of 1-butanol was refluxed overnight for 17 hours. Evaporation of the reaction mixture in vacuo gave a residual oil which was crystallized by trituration with water. The crude yellow solid was recrystallized from methanol-water to give 1.61 g (90.1%), mp 185°–188°, of crystalline product. The analytical sample was obtained by recrystallization from methanol-water; yield, 1.36 g (76.9%); mp 188°–191°.

METHOD B

6-Chloro-9-(3,4-dimethoxybenzyl)purine

To a suspension of 15.6 g (52.8 mmols) of 5-amino-4-chloro-6-(3,4-dimethoxybenzylamino)pyrimidine in 100 ml of triethyl orthoformate was added 149 mg (1.36 mmols) of ethanesulfonic acid and the resulting mixture was heated at 80° for 15 min. Upon cooling and addition of hexane to the reaction mixture, a yellow precipitate formed which was collected by filtration; yield, 15.4 g (95.6%) mp 159°–163°. Recrystallization from EtOH—H$_2$O gave the analytical sample; yield 13.2 g (82.2%) mp 160°–164°.

METHOD C

9-Veratryl-9H-adienine

In a steel bomb was heated a mixture of 4.00 g (13.1 mmols) of 6-chloro-9-veratrylpurine and 20 ml of liquid NH$_3$ for 17 hours at 54°. The excess NH$_3$ was allowed to evaporate and the white solid residue was recrystallized from EtOH—H$_2$O to give the crude product; yield 3.42 g (91.3%) mp 191°–193°. The analytical sample was obtained by a second recrystallization from EtOH—H$_2$O giving 2.33 g (62.3%) mp 192°–194°.

METHOD D

6-Propylamino-9-veratrylpurine

A reaction mixture containing 5.14 g (16.8 mmol) of 6-chloro-9-veratrylpurine, 7.0 ml (84.9 mmol) of propylamine and 60 ml of EtOH was refluxed for 2.5 hrs. Evaporation of the reaction mixture gave a residual solid which was recrystallized from acetone to give the crude product; yield 4.78 g (87.0%) mp 117°–120°. Further recrystallizations of the crude white material from acetone gave the analytical material; mp 122°–125°.

METHOD E

9-(3,4-Dimethylbenzyl)adenine (W10,813).

An ice cold suspension containing adenine (10.0 g, 74 mmol), 3.74 g (89.0 mmol) of NaH (57% suspension in oil) and 120 ml of DMF was allowed to reach RT and stirred for one additional hour. 3,4-Dimethylbenzyl chloride 13.7 g (89 mmol) was added to the reaction mixture. The resultant mixture was allowed to react at RT for 17 hrs with stirring. The reaction mixture was cooled and the resultant precipitate was collected by filtration giving the crude reaction product. Recrystallization of the crude white solid from methanol gave 3.90 g (21%) of white crystalline material; mp 206°–209°. The analytical sample was obtained by recrystallization from methanol; mp 211°–213°.

Anal. Calcd for C$_{14}$H$_{15}$N$_5$: C, 66.38; H, 5.97; N, 27.65. Found: C, 66.38; H, 6.10; N, 27.80.

I claim:
1. A compound of the formula II:

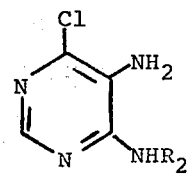

wherein R$_2$ is naphthyl alkyl of 1 to 3 carbons or phenyl alkyl of 1 to 3 carbons substituted in the aryl moiety by one or two alkoxy of 1 to 6 carbons or one or two chloro.

2. A compound according to claim 1 in which R$_2$ is 3,4-dimethoxybenzyl.

3. A compound according to claim 1 in which R$_2$ is 2-(3,4-dimethoxyphenyl)ethyl.

4. A compound according to claim 1 in which R$_2$ is 1-naphthylmethyl.

5. A compound according to claim 1 in which R$_2$ is 3,4-dichlorobenzyl.

* * * * *